United States Patent
James et al.

(10) Patent No.: US 8,960,190 B2
(45) Date of Patent: Feb. 24, 2015

(54) PROTECTIVE DEVICE

(75) Inventors: John Paul James, Rugby (GB); James Prince Love, Coventry (GB); David John Maudsley, Kenilworth (GB)

(73) Assignee: Medi-Immune Ltd., Rugby (GB)

( * ) Notice: Subject to any disclaimer, the term of this patent is extended or adjusted under 35 U.S.C. 154(b) by 605 days.

(21) Appl. No.: 12/594,388

(22) PCT Filed: Apr. 3, 2008

(86) PCT No.: PCT/GB2008/001195
§ 371 (c)(1),
(2), (4) Date: Mar. 25, 2010

(87) PCT Pub. No.: WO2008/120005
PCT Pub. Date: Oct. 9, 2008

(65) Prior Publication Data
US 2010/0175694 A1     Jul. 15, 2010

(30) Foreign Application Priority Data
Apr. 3, 2007 (GB) .................................. 0706507.1

(51) Int. Cl.
| | | |
|---|---|---|
| *A61M 16/06* | (2006.01) | |
| *A62B 7/00* | (2006.01) | |
| *A61L 9/20* | (2006.01) | |
| *A61L 9/16* | (2006.01) | |
| *A61L 9/18* | (2006.01) | |
| *A61L 9/22* | (2006.01) | |
| *A61M 16/10* | (2006.01) | |
| *A61M 16/00* | (2006.01) | |
| *A62B 18/02* | (2006.01) | |

(52) U.S. Cl.
CPC ... *A61L 9/16* (2013.01); *A61L 9/18* (2013.01); *A61L 9/20* (2013.01); *A61L 9/22* (2013.01); *A61M 16/10* (2013.01); *A61M 2016/0027* (2013.01); *A61M 2016/0039* (2013.01); *A61M 2202/203* (2013.01); *A61M 2202/206* (2013.01); *A61M 2205/053* (2013.01); *A62B 18/02* (2013.01)
USPC .................... 128/202.25; 128/206.12; 422/24

(58) Field of Classification Search
USPC ............. 128/201.25, 205.27, 206.12–206.14, 128/206.17; 422/24, 186.3
See application file for complete search history.

(56) References Cited

U.S. PATENT DOCUMENTS 5,037,618 A * 8/1991 Hager ...................... 422/186.03
5,165,395 A * 11/1992 Ricci ........................ 128/202.22
(Continued)

FOREIGN PATENT DOCUMENTS

DE            101 07 443 A1     8/2002
WO    WO 2004/033044 A1     4/2004

*Primary Examiner* — Quynh-Nhu H Vu
(74) *Attorney, Agent, or Firm* — Cantor Colburn LLP (57) ABSTRACT

A protective device protects the user from infection and may simultaneously immunize the user against future infection. In an embodiment, the protective device includes a disinfection chamber wherein the chamber is arranged to disinfect and/or sterilize fluid in the chamber prior to discharge of the fluid from the chamber such that the fluid discharged from the chamber comprises inactive microorganisms. The device may include a disinfection chamber in fluid communication with a face mask, with the chamber arranged to disinfect and/or sterilize fluid in the chamber prior to discharge of the fluid from the chamber to the mask, such that the fluid discharged from the chamber to the mask comprises inactive microorganisms.

10 Claims, 3 Drawing Sheets

(56) References Cited

U.S. PATENT DOCUMENTS

| | | | |
|---|---|---|---|
| 5,927,304 A * | 7/1999 | Wen | 134/153 |
| 6,328,937 B1 * | 12/2001 | Glazman | 422/186.3 |
| 2004/0031762 A1 * | 2/2004 | Ried | 210/748 |
| 2004/0051056 A1 * | 3/2004 | Disabito et al. | 250/504 R |
| 2007/0053188 A1 | 3/2007 | New et al. | |
| 2007/0102280 A1 * | 5/2007 | Hunter et al. | 204/157.15 |
| 2009/0133582 A1 * | 5/2009 | Snowball | 96/224 |

* cited by examiner

PROTECTIVE DEVICE

CROSS-REFERENCE TO RELATED APPLICATIONS

This application is the U.S. National Stage of International Application No. PCT/GB2008/001195, filed Apr. 3, 2008.

TECHNICAL FIELD

The invention relates to a protective device such as a face mask. The device protects the user from infection and may simultaneously immunise the user against future infection.

BACKGROUND TO THE INVENTION

People are frequently at risk of being infected by airborne pathogens. For the general population, common pathogens include common cold viruses (e.g. rhinoviruses) and influenza virus. Sub-groups of the population, such as hospital patients and hospital employees, may be exposed to, and therefore be at risk of infection by, other pathogens for example Methicillin Resistant *Staphylococcus aureus* (MRSA) or *Mycobacterium tuberculosis* (TB). Hospitalised patients are particularly likely to have some level of immuno-suppression, such as elderly people, people with congenital immunodeficiency, people undergoing or shortly following cancer treatment or organ transplantation, and therefore be susceptible to infection. Current methods of preventing infections include vaccination of at-risk groups and/or the wearing of personal protective equipment (PPE) such as face masks which include air filters.

There are drawbacks associated with vaccinating at-risk groups against infection. For example, it is not always possible to know which pathogens are likely to be present. Also, it can be difficult to predict the general type and precise strain of pathogen which is likely to occur. Furthermore, it can be difficult to ensure that all at-risk people are vaccinated. Also, there might not be a vaccine available for the infectious organism in question; and a vaccine may not be suitable for certain groups of people such as immuno-suppressed individuals.

Current personal protective equipment includes face masks such as surgical masks and P3 face masks. Such masks include air filters. Examples of face masks include the FFP3 cone style face mask with valve. Such a mask typically has a polymer outer facing which is lightweight and offers good breathability. The polymer outer facing may be ethylene propylene diene monomer (EPDM) rubber. The mask also typically has a melt blown filter media which has a bacterial filter efficiency of 99% for bacteria of 3 μm size. This provides good protection from air-borne bacteria. The mask also typically has a particle filtration efficiency of 99% for 0.3 μm particles and a differential pressure (delta P) of less than 6. This provides good breathability. The air valve is typically a one-way plastic valve which provides comfort and ease of breathing. The mask also typically includes a compliant cuff of a soft, latex-free material which provides a seal between the mask and the face of the user with good skin comfort. These masks provide a physical barrier between the user and the air and therefore prevent bacteria from being breathed in by the user. The masks also have a tendency to become blocked which causes breathing difficulties and can result in the mask leaking thus allowing bacteria to enter the user.

Chinese patent application CN1600383 discloses equipment for isolating and sterilizing infectious diseases to prevent release of the infectious disease from a patient to the environment. The equipment combines a filter with a high-voltage electrostatic field, a sterilizing UV lamp, an uninterruptible power supply and an electronic monitor with a microprocessor. This has the result that infectious particles are removed from the air. The equipment of CN1600383 is large.

Surgical masks are disposable devices that cover the mouth and nose of a care-giver during medical procedures. They help protect a care-giver against micro-organisms, body fluids, and small particles in the air by filtering the air before it is delivered to the care-giver. Furthermore, they protect the patient from inhaling micro-organisms and body fluids which may be exhaled by the care-giver. A problem of such masks is that they have a high resistance against air and can therefore make breathing difficult. Furthermore, if not fitted carefully to the face of the user, such masks leak and therefore do not provide the protection expected and required. They also provide limited or no protection against pathogens transmitted as aerosols, that is particles with sizes of less than or equal to 5 μm diameter.

Current devices work by preventing microorganisms from contacting and/or being inhaled by the user of the device. That is, the devices are configured to prevent microorganisms from exiting the device. Such prevention may be achieved through the inclusion of a barrier such as a filter. A disadvantage of use of a filter is that it may become clogged and therefore prevent air from passing through the filter and or result in leakage around the filter thus allowing microorganisms to pass around the filter and consequently reach the user and thus rendering the device useless.

SUMMARY OF THE INVENTION

What is needed is an improved device which protects the user of the device against infection from airborne micro-organisms including pathogens. It is preferred that the device simultaneously immunizes the user thereby protecting the user against subsequent exposure to the micro-organism. In the present invention, the micro-organism(s) in the air are disabled rather than physically removed from the air. The term 'disabled' includes reduction of pathogenicity and/or virulence of the micro-organism. The term 'air' includes air that is generally inhaled and other fluids such as gases or mixtures of gases. The term 'user' includes (a) a direct user of the device, for example a person inhaling air directly from the device via a face mask and (b) an indirect user of the device, for example a person inhaling air expelled from the device.

The invention is based in part on the realisation that if a device that is used to sterilise air allows, or is designed to allow, inactivated microorganisms to be delivered to a user of the device, then exposure of the user of the device to the inactivated ("disabled") microorganism may provide protection to the user from infection from active forms of the same or related microorganisms. This protection might be immunological, for example through a humoral and/or cellular response or by another mechanism, for example by blocking attachment of the live microorganism to a target cell in the body of a user of the device.

A further aspect of the invention is based in part on the passage of DI virus through a device used to sterilise air thus potentially providing protection from intact related virus.

The invention relates to a device and to a method and a use of the device.

The terms 'pathogen' and 'micro-organism' include algae, protozoa, fungi, bacteria, *rickettsia*, viruses and spores of these.

Therefore a first aspect of the invention provides a protective device comprising a disinfection chamber wherein the chamber is arranged to disinfect and/or sterilize fluid in the chamber prior to discharge of the fluid from the chamber such that the fluid discharged from the chamber comprises inactive microorganisms.

The protective device may comprise a disinfection and/or sterilization chamber in fluid communication with a face mask wherein the chamber is arranged to disinfect and/or sterilize fluid in the chamber prior to discharge of the fluid (i) from the chamber to the mask and/or (ii) from the chamber to the external environment. Preferably the device is configured such that the fluid discharged from the chamber to the mask comprises inactive microorganisms.

Preferably the inactive microorganisms comprise antigen capable of conferring immune protection on a recipient of the fluid.

It is preferred that the inactive microorganisms are capable of blocking, inhibiting and/or interfering with infection of a recipient of the fluid by a live or active microorganism.

Ideally, the inactive microorganism blocks binding of the live or active microorganism to a cell of the recipient of the fluid.

Preferably the microorganisms to be delivered to the recipient of the device comprise defective-interfering (DI) virus.

The fluid is preferably taken in from the surrounding environment and/or air exhaled from a subject, such as a patient, or another user.

Preferably, the face mask covers both the nose and mouth of the user. Face masks may further cover other parts of the user, for example the eyes and/or the full head of the user.

The face mask is preferably for a human user but may also be applicable to non-human users such as animals including mammals and especially domestic pets and livestock.

Preferably the face mask does not comprise a filter, such as a bacterial or viral filter.

The term 'disinfection' is used to mean decreasing the infectivity of micro-organisms present. It particularly relates to decreasing the infectivity of pathogenic micro-organisms present. Preferably, the number of infectious micro-organisms and/or the infectivity of the micro-organisms is reduced to at least $10^{-1}$, $10^{-2}$, $10^{-3}$, $10^{-4}$, $10^{-5}$, $10^{-6}$, $10^{-6}$, $10^{-8}$, or $10^{-9}$ of the original value. Most preferably the infectivity of the organism(s) is reduced to zero. The term 'sterilization' is used to mean removing the reproductive powers of microorganisms present. It particularly relates to decreasing the reproductive powers of infectious and/or pathogenic microorganisms present. Preferably, the reproductive power of micro-organisms is reduced to at least $10^{-1}$, $10^{-2}$, $10^{-3}$, $10^{-4}$, $10^{-5}$, $10^{-6}$, $10^{-7}$, $10^{-8}$, or $10^{-9}$ of the original value. Most preferably the reproductive powers of the organism(s) are reduced to zero.

Preferably there is sterilization, by the device, of aerosol-borne infectious organisms and/or particulate-borne organisms.

The terms 'disinfection' and 'sterilization' are covered by the term 'inactivation'.

Disinfection and/or sterilization may be carried out by any suitable means including UV irradiation, plasma, microwave and/or ultrasound. Preferably the disinfection and/or sterilization chamber comprises a disinfection and/or sterilization agent selected from UV, plasma, microwave and/or ultrasound. Preferably the sterilizing agent is UV.

It is known that defective interfering (DI) viruses arise on culture of many virus types including influenza virus. It is also known that DI viruses are much more resistant to UV than intact virus. It is further known that DI viruses inhibit or interfere with intact virus, thus providing protection against exposure to an intact virus. In the present invention, the UV dose is preferably such that intact virus is disabled and DI viruses are left largely unaffected thus potentially allowing them to provide protection to the user. For example, an appropriate UV dose is one which reduces virus infectivity to $10^{-3}$ and also allows active DI viruses to survive.

Preferably the UV dose is such that it effectively sterilises the microorganisms, except DI viruses, present in the chamber while at the same time allowing largely undamaged DI viruses to survive. That is, the surviving virus is interfering virus that is still biologically active such that it is able, for example, to prevent death in mice given a lethal dose of virus, or to effect plaque reduction in a plaque assay. Preferably at least 10, 20, 30, 40, 50, 60, 70, 80, 85, 90, 95 or 100% of DI viruses are allowed to survive. A UV dose may be applied to the virus such that normal virus (i.e. non-DI virus) is reduced to $10^{-6}$ compared to the levels prior to application of UV.

In one preferred embodiment, the device comprises an outer tube and a sterilization and/or disinfection source located at least partially within the tube. Preferably the source is selected from UV, plasma, microwave and/or ultrasound. Preferably, the outer tube comprises a reflective component—for example the outer tube may comprise an inner coating of reflective material. Preferably the reflective component is present within the outer tube. Preferably the reflective material is selected from mirrored glass or mirrored plastic or other suitable reflective material. The reflective material may comprise aluminium, such as polished aluminium, for example a polished aluminium internal coating or internal face of the chamber. Preferably the reflective material reflects at least 75% of the UV, plasma, microwave and/or ultrasound to which it is exposed. More preferably, the reflective material reflects at least 80, 85, 90, 95, or 100% of the UV, plasma, microwave and/or ultrasound to which it is exposed.

The fluid being sterilized may be separated from a source of sterilization (such as a UV tube) by material transparent to the sterilizing agent (e.g. UV). Thus a UV lamp and/or LED may be located outside of the chamber/tube whilst allowing UV to be delivered into the chamber/tube. This provides the advantage of reducing loss of sterilized material in the chamber. Also, such an arrangement allows air to flow uninhibited by the lamp and/or LED since the lamp and/or LED may be located exterior to the chamber. The transparent coating can also protect the lamp and/or LED from exposure to pathogen.

For example, the tube may comprise quartz and/or Teflon.

For example, the lamp and/or LED may be located in a Teflon tube around which the air flows. The lamp (and/or LED) and Teflon tube may be located within a reflective outer tube.

Inclusion of a reflective material allows the amount of UV, plasma, microwave and/or ultrasound emitted from a source to be magnified thus allowing a higher intensity to be delivered than initially emitted.

For example, with a reflective material with a reflective power of 80%, the effective intensity increases on one reflection to 1.8 times the originally emitted intensity and after several reflections to generate an effective dose of many times, for example up to 4.5 times, the original emitted intensity. Therefore, an initial intensity of 200 W/m² can easily be magnified to an effective intensity of 900 W/m². An advantage of magnifying the intensity is that it allows delivery of a dose of UV, plasma, microwave and/or ultrasound sufficient for disinfection and/or sterilization of microorganisms over shorter time periods compared with non-magnification.

Preferably there is a gap between the outer tube and the UV source, preferably this is from 0.1 mm to 3 cm, more preferably, from 0.1 cm to 1 cm.

Preferably the chamber has a maximum volume of from 250 to 1000 ml, more preferably 700 ml.

Preferably, the UV source is selected from a fluorescent lamp and a light emitting diode. (LED) More preferably the fluorescent lamp is a low pressure mercury discharge lamp. Preferably the UV source is in the form of a tube, such as a TUV lamp. Preferably the lamp has electrical connections at one end. Preferably the UV source is High Output. A High Output lamp is one with a higher wattage than is normal for its linear dimension. This may be due, for example, to increased airflow and/or to decreased temperature. Although actual output from the lamp is not dependent upon air-flow, the output required to achieve the required intensity and/or dose is dependent upon air-flow.

A preferred UV source is capable of emitting at a wavelength of from 240 nm to 300 nm. Preferably the wavelength is selected from 240, 250, 260, 270, 280, 290 and 300 nm. Most preferably the wavelength is 250 nm or 254 nm or 265 nm. Particularly preferred lamps include TUV 4WT5, TUV 6WT5, TUV 8WT5, TUV 10WT5, TUV11WT5, TUV15WT5, TUV16WT5, TUV 25WT8, TUV 30WT8, TUV 36WT8, TUV 55W HO T8, TUV 75W HO T8, TUV115W VHO T12, TUV 240 W XPT, TUV 270 W XPT, TUV PL-S 5W, TUV PL-S 9W, TUV PL-S 11W, TUV PL-L 18W, TUV PL-L 35W HO, TUV PL-L 36W, TUV PL-L 55W, TUV PL-L 95W HO, TUV 36 T5, TUV 64 T5, TUV 36T5 HO and TUV 64T5 HO (available from Philips, Eindhoven, The Netherlands). The dose of UV required to inactivate a micro-organism is related to the size of the genome of the micro-organism. Micro-organisms with large genomes can be inactivated by relatively low levels of UV. Micro-organisms with small genomes require higher levels of UV to be inactivated.

One or more lamps and/or LEDs may be used, for example 1, 2, 3, 4 or 5 lamps and/or LEDs.

UV dose ($J/m^2$) is related to the intensity ($W/m^2$) of the UV and the time of exposure (seconds). For a constant intensity, increasing the time of exposure will increase the dose.

Survival of micro-organisms when exposed to UV radiation is given by the approximation $$N_t/N_0 = \exp(-kE_{\it eff}t) \quad \text{(Equation 1)}$$

$$\text{Hence } \ln N_t/N_0 = -kE_{\it eff}t \quad \text{(Equation 2)}$$

$N_t$ is the number of germs at time t; $N_0$ is the number of germs before exposure; K is a rate constant depending on the species; $E_{\it eff}$ is the effective irradiance in $W/m^2$. The product $E_{\it eff}t$ is called the effective dose $H_{\it eff}$ and is expressed in $W \cdot s/m^2$ of $J/m^2$. Therefore, for 90% kill, Equation 2 becomes $2.303 = kH_{\it eff}$. Some k value indicators are given in Table 1 (below) where they can be seen to vary from 0.2 $m^2/J$ for viruses and bacteria to $2 \times 10^{-3}$ for mould spores and $8 \times 10^{-4}$ for algae. These data can be used to plot survival curves for micro-organisms with respect to UV dose.

TABLE 1

UV doses ($J/m^2$) for 10% survival of micro-organisms exposed to 254 nm radiation and rate constant k ($m^2/J$)
(information obtained from UV Disinfection - Application Information, Philips, Eindhoven, The Netherlands). January 2004).

| | Dose ($J/m^2$) | K ($m^2/J$) |
|---|---|---|
| Bacteria | | |
| Bacillus anthracis | 45.2 | 0.051 |
| B. megatherium sp. (spores) | 27.3 | 0.084 |
| B. megatherium sp. (veg) | 13.0 | 0.178 |
| B. parathyphosus | 32.0 | 0.072 |
| B. subtilis | 71.0 | 0.032 |
| B. subtilis spores | 120.0 | 0.019 |
| Campylobacter jejuni | 11.0 | 0.209 |
| Clostridium tetani | 120.0 | 0.019 |
| Corynebacterium diphteriae | 33.7 | 0.069 |
| Dysentery bacilli | 22.0 | 0.105 |
| Eberthella typhosa | 21.4 | 0.108 |
| Escherichia coli | 30.0 | 0.077 |
| Klebsiella terrifani | 26.0 | 0.089 |
| Legionella pneumophila | 9.0 | 0.256 |
| Micrococcus candidus | 60.5 | 0.038 |
| Micrococcus sphaeroides | 100.0 | 0.023 |
| Mycobacterium tuberculosis | 60.0 | 0.038 |
| Neisseria catarrhalis | 44.0 | 0.053 |
| Phytomonas tumefaciens | 44.0 | 0.053 |
| Pseudomonas aeruginosa | 55.0 | 0.042 |
| Pseudomonas fluorescens | 35.0 | 0.065 |
| Proteus vulgaris | 26.4 | 0.086 |
| Salmonella enteritidis | 40.0 | 0.058 |
| Salmonella paratyphi | 32.0 | 0.072 |
| Salmonella typhimurium | 80.0 | 0.029 |
| Sarcina lutea | 197.0 | 0.012 |
| Seratia marcescens | 24.2 | 0.095 |
| Shigella paradysenteriae | 16.3 | 0.141 |
| Shigella sonnei | 30.0 | 0.077 |
| Spirillum rubrum | 44.0 | 0.053 |
| Staphylococcus albus | 18.4 | 0.126 |
| Staphylococcus aureus | 26.0 | 0.086 |
| Streptococcus faecalis | 44.0 | 0.052 |
| Streptococcus hemoluticus | 21.6 | 0.106 |
| Streptococcus lactus | 61.5 | 0.037 |
| Streptococcus viridans | 20.0 | 0.115 |
| S. entertidis | 40.0 | 0.057 |
| Vibrio chlolerae (V. comma) | 35.0 | 0.066 |
| Yersinia enterocolitica | 11.0 | 0.209 |
| Yeasts | | |
| Bakers' yeast | 39 | 0.060 |
| Brewers' yeast | 33 | 0.070 |
| Common yeast cake | 60 | 0.038 |
| Saccharomyces cerevisiae | 60 | 0.038 |
| Saccharomyces ellipsoideus | 60 | 0.038 |
| Saccharomyces sp. | 80 | 0.029 |
| Mould spores | | |
| Aspergillus flavus | 600 | 0.003 |
| Aspergillus glaucus | 440 | 0.004 |
| Aspergillus niger | 1320 | 0.0014 |
| Mucor racemosus A | 170 | 0.013 |
| Mucor racemosus B | 170 | 0.013 |
| Oospora lactis | 50 | 0.046 |
| Penicillium digitatum | 440 | 0.004 |
| Penicillium expansum | 130 | 0.018 |
| Penicillium roqueforti | 130 | 0.018 |
| Rhizopus nigricans | 1110 | 0.002 |
| Virus | | |
| Hepatitis A | 73 | 0.032 |
| Influenza virus | 36 | 0.064 |
| MS-2 Coliphase | 186 | 0.012 |
| Polio virus | 58 | 0.040 |
| Rotavirus | 81 | 0.028 |
| Protozoa | | |
| Cryptosporidium parvum | 25 | 0.092 |
| Giardia lamblia | 11 | 0.209 |
| Algae | | |
| Blue Green | 3000 | 0.0008 |
| Chlorella vulgaris | 120 | 0.019 |

Preferably, the UV source is capable of emitting and/or delivering UV at an intensity of from 75 to 350 $W/m^2$. Particularly levels of UV emitted and/or delivered are 75 to 350 W/m$^2$, more preferably from 75 to 100, 100 to 125, 125 to 150, 150 to 175, 175 to 200, 200 to 225, 225 to 250, 250 to 275, 275 to 300 J/m$^2$, 300 to 325 W/m$^2$ and/or 325 to 350 W/m$^2$.

Other preferred ranges include 100-350 W/m$^2$, 150-525 W/m$^2$ and 250-875 W/m$^2$, 100-525 W/m$^2$, 150-875 W/m$^2$ and 100-875 W/m$^2$.

Preferred doses include: Bacteria: 5 to 200 J/m$^2$, Yeasts: 30 to 90 J/m$^2$, Moulds: 50 to 1350 J/m$^2$, Viruses: 30 to 190 J/m$^2$, Protozoa: 10 to 30 J/m$^2$, *Rickettsia:* 100 to 3000 J/m$^2$.

Preferably the UV is delivered over a short time period, preferably less than 2 seconds, more preferably less than 1 second, for example less than 0.25 seconds, most preferably about 0.5 seconds. Preferably the intensity and/or dose delivered is sufficient to reduce the infectivity and/or reproductive powers of microorganisms present to from less than 0.05 (i.e. 95% reduction), less than 0.01 (i.e. 99% reduction), $10^{-3}$ to $10^{-9}$, especially to $10^{-3}$, $10^{-4}$, $10^{-5}$, $10^{-6}$, $10^{-7}$, $10^{-8}$ or $10^{-9}$.

Assuming that the effective radiation from the source (e.g. UV light) is 80% of that emitted, preferred dose ranges can be calculated by multiplying the parameters for the preferred dose ranges, above, by 0.8. This assumption is based on there being no reflectance of the radiation. If reflectance occurs, the effective radiation can be higher.

Exposure of a virus to a UV may result in disinfection and/or sterilization of virus, but not the inactivation of any defective interfering (DI) virus present. These defective interfering particles can interfere with the spread of intact virus, which may be pathogenic, and thus provide some protection from the virus. The defective interfering particles cannot replicate on their own because they require the presence of the full virus in order to replicate. Therefore, defective interfering particles pose no safety threat on their own. Hence the device and/or method of the present invention are preferably designed to provide additional protection against future exposure to the same or similar viruses. In cells, DI viruses have a half-life typically in the region of 3 weeks and therefore provide protection for a period of time following the initial exposure of a subject to the DI virus.

An advantage of treating air with, for example, UV microwave, ultrasound and/or plasma is that, following exposure of the air to one or more of these sources, micro-organisms and/or fragments of micro-organisms which are of reduced or zero infectivity remain present in the air and are expelled from the chamber with the air. Exposure of a subject to such micro-organisms and/or fragments results in exposure of the subject to antigenic determinants of the micro-organisms and/or fragments of micro-organisms. Exposure to inhaled antigen can both confer protective immunity on the subject inhaling the antigen and also enable the subject to mount a more rapid and effective immune response to any future exposure to the micro-organism.

Delivery of antigen via a face mask would primarily deliver the antigen to the nasal passages and/or lungs of the user. An additional advantage of delivery in this way is that it expected to promote a preference for an immunoglobulin A (IgA) immune response. This is the most appropriate type of immune response to provide protection against pathogens that typically gain access via the inhaled route, or through any mucosal site such as nasal or gut linings. Furthermore, there is evidence that immunization via the inhalation route produces an immune response that provides protection not just against the immunising pathogen but also against related and/or similar pathogens. In addition, delivery of antigen via the lungs may stimulate an immune response to an existing infection. Therefore use of the device may provide some therapeutic benefit for a subject already infected with a pathogen e.g. *Mycobacterium tuberculosis* (TB). The term 'related and/or similar' means a microorganism that is taxonomically related and/or a microorganism sharing one or more antigenic determinants with the microorganism to which it is related and/or similar.

Preferably, the device is configured to allow air to be transferred from the disinfection and/or sterilization chamber to the face mask to enable delivery of disinfected and/or sterilized air to a user of the face mask. Such device would be useful to protect a user of the device from micro-organisms present in the air. For example, the device could be used to protect medical staff from a subject, such as a patient, infected with micro-organisms which can be transmitted through the air.

Preferably the device is configured to allow antigens of the inactivated micro-organism to be transferred to the user.

It is preferred that least 0.5, 2, 5, 10, 20, 30, 40, 50, 60, 70, 75, 80, 85, 90, 95, more preferably 100% of the material inputted into the device is delivered from the device to the user.

Alternatively, or in addition, the device may be configured to allow air to be transferred from, for example, a face mask to the disinfection and/or sterilization chamber with the air being disinfected and/or sterilized prior to being expelled from the disinfection and/or sterilization chamber to the external environment. Such a device could be used by a user infected with micro-organisms which can be transmitted through the air. This would protect subjects in the vicinity of the infected user from micro-organisms exhaled from by the infected user. A further preferred feature is that the device may be configured to allow input of antigenic material to form a mixture of antigenic material and air. For example the device, preferably the chamber, may include one or more ports.

Preferably, the device is configured to provide a substantially constant disinfection and/or sterilization level. This ensures sterilisation while, in the case of DI virus being present, allowing maximum passage of active DI virus, thus maximising user protection. The air flow within the device may alter due to changes in the respiratory rate of the user. For example, the respiratory rate would increase during exercise. The respiratory rate would also increase on exposure to reduced oxygen levels. Increasing the respiratory rate would increase air-flow.

Preferably, the device is configured such that when the air-flow increases, the intensity and/or duration of disinfection and/or sterilization increases thus maintaining a substantially constant level of disinfection and/or sterilization. Sterilization and/or disinfection levels may be kept substantially constant, for example, by shading the UV source. For example, increasing the degree to which a UV source is shaded would decrease the dose of UV and decreasing the degree to which a UV source is shaded would increase the dose of UV. Alternatively, or in addition, the dose of UV supplied could be controlled, e.g. kept substantially constant, by providing a plurality of UV sources. Switching on all of the UV sources would provide a maximum dose. Switching off all of the UV sources would provide a zero dose. Switching on an intermediate number of the UV sources would provide an intermediate dose. For example UV light emitting diodes (LEDs) may be used. Preferably from 1 to 10 LEDs are used, from 1 to 20, from 1 to 100 or from 1 to 1000.

Alternatives to this mechanical control of the dosage include electrical control, for example, the use of a device to measure the air flow, e.g. a pitot tube, which feeds information into an electronic control which, in turn, adjusts the current supply to the lamp so that the optimum UV exposure is achieved. Further alternatives include an electronic control of the illumination levels in relation to air flow, e.g. by varying the voltage supplied to the UV source.

The above methods of controlling the UV dose may be used separately or in any combination.

Figure 2:
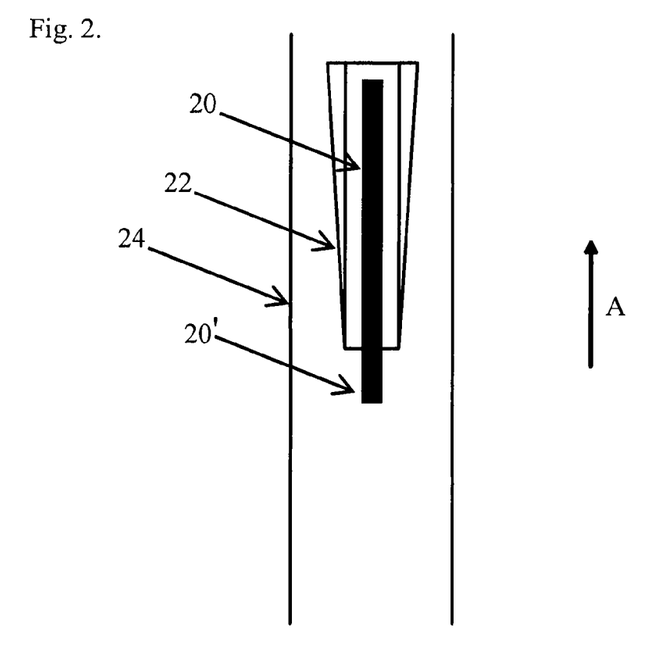
FIG. 2. is a schematic representation of a shading system for controlling the dose of UV delivered under low air-flow conditions.

When sterilization and/or disinfection is carried out using a UV source, it is preferred that the substantially constant disinfection and/or sterilization level is achieved by providing variable levels of shading to the UV source. For example, as air-flow into the chamber increases, preferably the level of shading of the UV source decreases. Conversely, as air-flow into the chamber decreases, preferably the level of shading of the UV source increases. For example, shading may be provided to alter the extent to which the UV source is exposed. A switch, such as a mechanical or electrical switch, may be used to control the amount of shading. The shading may be controlled between levels of from 0 to 100% exposure of the UV source. For example, shading may be controlled at from 10 to 20, 30, 40, 50, 60, 70, 80, 90 and/or 100%. Preferably the shade is conical. One example of shading is shown in FIG. 2. Alternatively, or in addition, a low pressure drop gas flow meter may be used to maintain a substantially constant disinfection and/or sterilization level. This is shown, by way of example, in FIG. 3.

Preferably, the device further comprises a power unit. The power unit may be configured for battery or mains power input. Alternatively, the power supply may be an integral battery that easily plugs in and can be replaced.

Preferably, the device is portable. For example, it is preferred that the size of the device is sufficiently small to be carried by a user. Carriage includes attachment to a user via a belt or strap such as a shoulder strap. Preferably, the device is adapted for carrying by a user.

A second aspect of the invention provides a method of providing disinfected and/or sterilized air to a user comprising:
  (a) receiving air within a chamber,
  (b) disinfecting and/or sterilizing the air,
  (c) delivering the disinfected and/or sterilized air to the user.

Preferably step (c) delivers the product of step (b) to the user. Preferably the air is delivered to the user via a face mask.

Preferably the air discharged from the chamber (i.e. the product of step (b)) comprises inactive microorganisms.

Preferably the inactive microorganisms comprise antigen capable of conferring immune protection on a recipient of the fluid.

It is preferred that the inactive microorganisms are capable of blocking, inhibiting and/or interfering with infection of a recipient of the fluid by a live or active microorganism.

Ideally, the inactive microorganism blocks binding of the live or active microorganism to a cell of the recipient of the fluid.

Preferably the microorganisms to be delivered to the user comprise defective-interfering (DI) virus.

Preferably, the air is disinfected and/or sterilized using a source selected from UV, microwave, ultrasound and/or plasma as described for the first aspect of the invention.

Preferably, the air is exposed to a UV dose which is sufficient to inactivate a live micro-organism but leaves at least some UV irradiated micro-organism a sufficiently active state expected to confer on the user some protection against future exposure to the live micro-organism. This protection may include immune protection. Preferably the micro-organism is a pathogen. Preferably the micro-organism is a virus. The irradiated virus may comprise a DI virus. 'Sufficiently active state to confer on the user some protection against future exposure to the live micro-organism' may include an inactive state.

During virus infection, small fragments of the viral nucleic acid can be formed and packaged into the virus particles being made. These defective interfering particles can interfere with the spread of the intact virus, which intact virus may be pathogenic, and thus provide some protection from the virus. The defective interfering particles cannot replicate on their own, because they require the presence of the full virus in order to replicate. Therefore, defective interfering particles pose no safety threat on their own.

Preferably the UV delivered inactivates any micro-organisms, including pathogens, present in the air, leaving antigen in the air which may be delivered by inhalation to the wearer of the mask and or by discharge from the mask to subjects in the vicinity. Exposure of a subject to antigen may generate an immune response. Such an immune response may be beneficial to a subject already infected (a curative or therapeutic response) or provide protection from, or reduce severity of (e.g. by increasing the speed of response) future exposure to a micro-organism, including a pathogen.

Preferably the UV doses are as described for the first aspect of the invention.

The method may further comprise inputting non-infectious antigenic material into the air, prior to delivery the user. 'Non-infectious' means antigenic material which is not sufficiently infectious to cause disease. Preferably, the non-infectious antigenic material is capable of eliciting a protective immune response in the user. Preferably the non-infectious antigenic material is derived from one or more micro-organisms such as bacteria, yeasts, moulds, viruses, protozoa, algae and spores of these micro-organisms.

Suitable antigenic material is described for the first aspect of the invention and may include vaccines suitable for oral and/or nasal delivery, such as vaccines for delivery via a nebulizer and/or other inhaler. Suitable vaccines include those providing protection against viruses or bacteria such as one or more of, influenza virus, Ebola virus, Severe Acute Respiratory Syndrome Virus, Smallpox and *Mycobacterium tuberculosis* (TB).

Preferably, the micro-organism is a pathogen, preferably the pathogen is selected from is selected from influenza virus, Ebola virus, Smallpox, and Severe Acute Respiratory Syndrome Virus. Preferably, the antigenic material is derived from a virus or bacterium such as influenza virus, Ebola virus and Severe Acute Respiratory Syndrome Virus, Smallpox, *Staphylococcus aureus* such as Methicillin Resistant *Staphylococcus aureus* (MRSA) *Mycobacterium tuberculosis* (TB) and *Bacillus anthracis*.

Alternatively, or in combination with inputting antigenic material, the method may further comprise inputting defective interfering (DI) virus into the air prior to delivery to the user. Preferably such DI virus is capable of providing some protection, and/or therapeutic benefit, to the user. Preferably the DI virus is related to a known virus threat or risk.

A third aspect of the invention relates to use of the method according to the second aspect of the invention to protect a user of the device from micro-organisms, especially pathogens, present in the environment of the user.

A fourth aspect of the invention relates to the use of a device as described herein to protect a user from pathogens present in the environment of the user.

According to the third and fourth aspects of the invention, alternatively, or in addition, the method and/or device may be used to protect a subject in the vicinity of the user of the device from micro-organisms being exhaled from that user.

For example, a device of the present invention may receive air from an infected user, disinfect and/or sterilize that air and then release the air into the environment. Thus a subject in the vicinity of that air would not come into contact with infected air emitted directly from the infected user. Preferably the use results in boosting the immune response of the user either to an existing infection and/or to future exposure to an infection.

Preferably the air discharged from the disinfection and/or sterilization chamber in the first, second, third and/or fourth aspect of the invention is at room temperature, preferably from 15° C. to 30° C., more preferably from 20° C. to 25° C. or from 15° C. to 20° C.

BRIEF DESCRIPTION OF THE DRAWINGS

The invention will now be described, by way of example only, with reference to the following figures:

FIG. 4. is a schematic diagram of a sterilization chamber comprising an internally polished aluminum tube.

DESCRIPTION OF PREFERRED EMBODIMENTS

Figure 1:
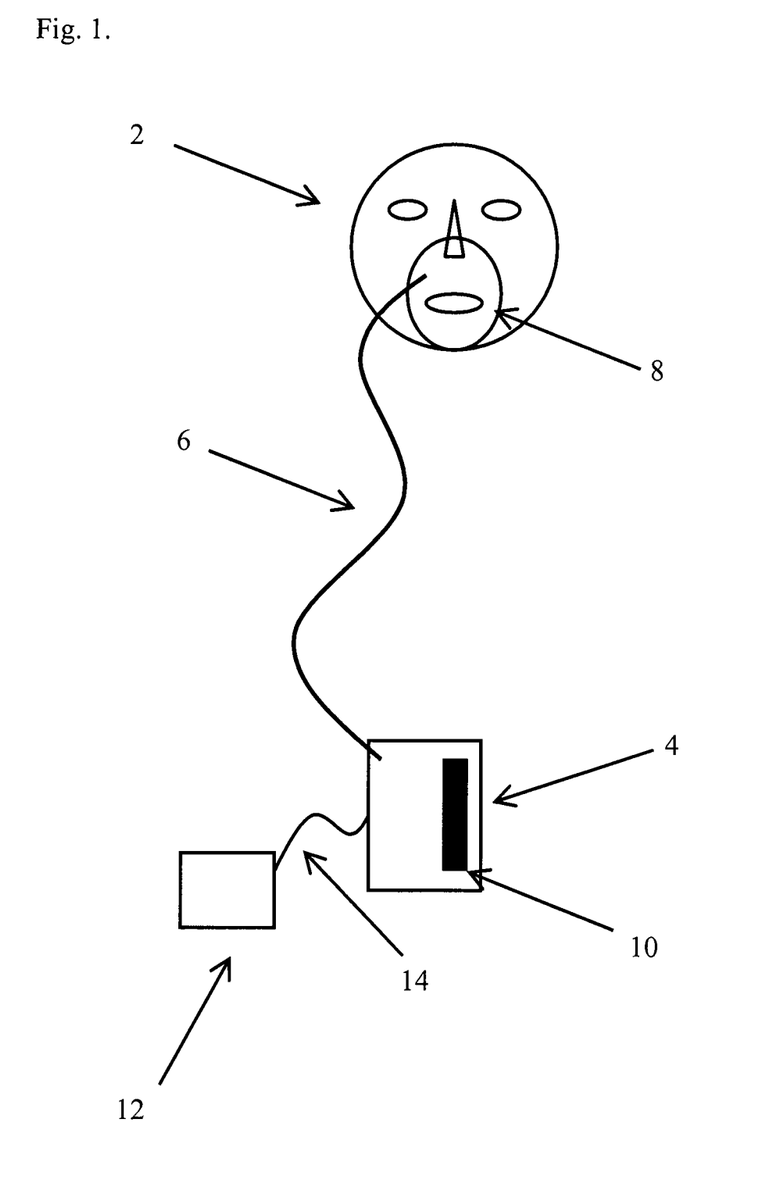
FIG. 1. is a schematic representation of a device comprising a face mask, disinfection chamber and power unit.

According to FIG. 1. there is provided a device for protecting a user 2 from airborne micro-organisms. The device comprises a disinfection chamber 4 from which tubing 6 extends.

The tubing 6 is connected to a face mask 8. The disinfection chamber 4 comprises a UV source 10. The disinfection chamber is connected to an external power supply 12 via cable 14.

FIG. 2. shows a shading system for controlling the dose of UV delivered from a UV source. UV source 20 is housed in shade 22 which in turn is encased in casing 24. The direction of the air-flow is shown by arrow A. Under low air-flow conditions, a relatively small part of UV source 20' is exposed from the shade. The intensity of UV delivered is related to the size of exposed part of the source. Therefore, a low intensity of UV is delivered.

As the air flow increases, the shade 22 rises against gravity and exposes more of UV source 20 to the air flowing round the outside of the shade. The casing 24 containing the lamp 20 and shade 22 opens slightly so that when the shade 22 rises the cross-section between the shade and chamber increases. The top of the shade 22 is closed.

Figure 3:
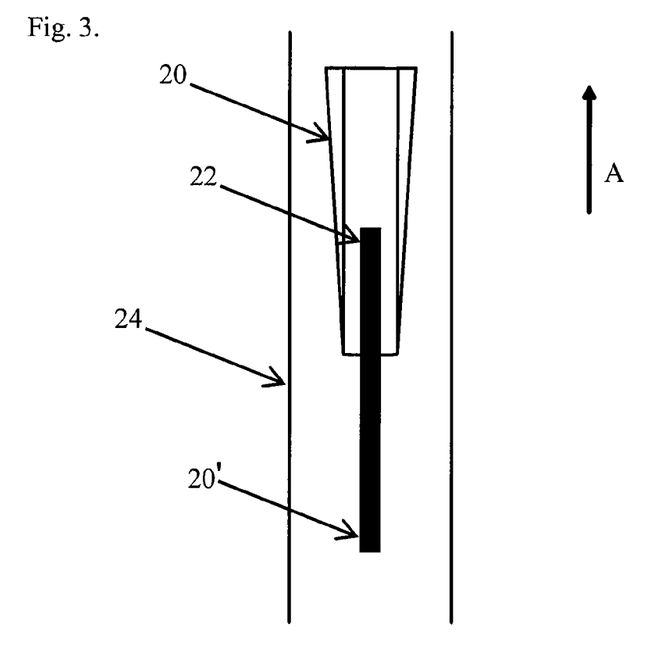
FIG. 3. is a schematic representation of a shading system for controlling the dose of UV delivered under high air-flow conditions.

FIG. 3. shows the same shading system as described for FIG. 2. UV source 20 is housed in shade 22 which in turn is encased in casing 24. The direction of the air-flow is shown by arrow A. Under high air-flow conditions, a relatively large part of UV source 20' is exposed from the shade. The intensity of UV delivered is related to the size of exposed part of the source. Therefore, a large intensity of UV is delivered, thus keeping the dose relatively constant.

Figure 4A:
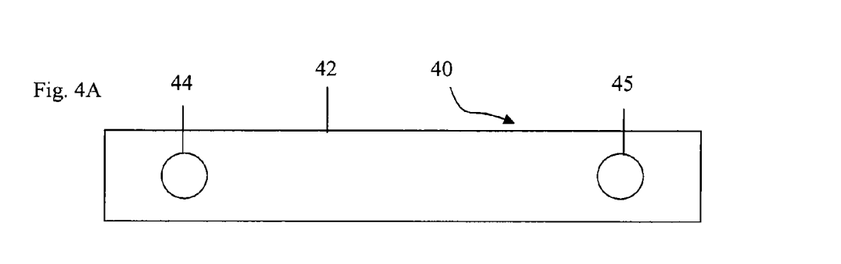
FIG. 4A is a side view.
Figure 4B:
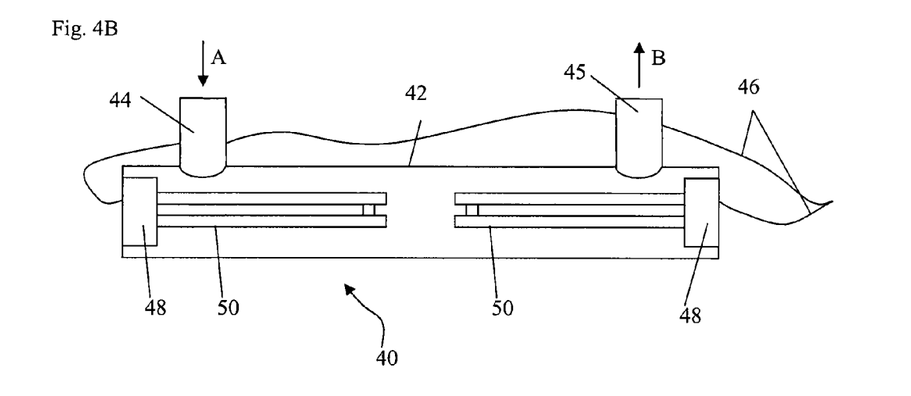
FIG. 4B is a longitudinal cross-section.

According to FIG. 4. there is provided a disinfection chamber (40) for a device for protecting a user from airborne micro-organisms. The disinfection chamber (40) comprises a tube (42), an air-inlet (44) and an air outlet (45). The tube (42) comprises an aluminium tube, the internal face of which is polished to a mirror finish. At each short end of the tube, there are bulb sockets (48) for housing UV bulbs (50). Power cables (46) are connected to the sockets via end-caps (not shown) of the tube. Air enters the device in the direction of arrow A and exits the device in the direction of arrow B. The device may be connected to a mask.

EXAMPLES

The invention is further illustrated by the following non-limiting examples:

Example 1

By way of example, influenza virus, *Streptococcus faecalis* and *Clostridium tetani* were irradiated using one TUV PL-S 9W lamp (Philips, Eindhoven, The Netherlands) with a length of 0.21 meters and effective radiance of 76.22 W/m$^2$ and a known effective dose ($H_{eff}$). The time for effective kill rate was measured and is shown in Table 2 (below).

TABLE 2

| Time taken for effective kill of target microorganisms. | | | | | |
| --- | --- | --- | --- | --- | --- |
| Target organism | Lamp type | Lamp length, L (m) | Distance from Lamp, a (m) | Effective irradiance E (W/m$^2$) | $H_{eff}$ Effective dose (J/m$^2$) | Time for effective kill rate (sec) |
| Influenza virus | TUV PL-S 9W | 0.21 | 0.025 | 76.22 | 36.0 | 0.47 |
| Streptococcus faecalis | TUV PL-S 9W | 0.21 | 0.025 | 76.22 | 44.3 | 0.58 |
| Clostridium tetani | TUV PL-S 9W | 0.21 | 0.025 | 76.22 | 121.2 | 1.59 |

The kill time would decrease if more than one lamp was used. For example, use of two lamps would halve the kill time.

Example 2

This example illustrates the basic device and also the apparatus used for measuring the effectiveness of such devices.

A chamber was constructed comprising a tube of rectangular cross section with two UV lamps mounted in the middle. The connectors for the lamps were arranged back to back in the centre of the tube with the lamps pointing towards the ends. Two connecting tubes were attached to the ends of the chamber to allow air to flow in and our respectively. The device comprised no filter, no foam and no baffles and therefore was designed to allow sterilized microorganisms to pass through the chamber.

The device was tested first by passing an aerosol of Coomassie blue dye through the chamber and inspecting the chamber for leaks and any deposition of dye. Dye was observed to be deposited on the inside of the chamber especially around the lamp fittings and most particularly in the 90 degree angles and corners of the chamber where the walls meet each other.

These results illustrate that passage of inactivated microorganisms through a UV sterilising device does not inevitably occur even in the absence of a filter. That is, some microorganisms are trapped in the device and are not emitted from the device.

The testing apparatus was set up as follows: a source of air flow (in this case a compressed air cylinder, but a fan, pump, vacuum pump could be used as an addition or as an alternative) was connected to the device. A nebuliser was connected to the inlet tube so as to input aerosol into the air flowing in. Air flowing out of the output tube was bubbled through 1000 ml phosphate buffered saline (PBS) so as to collect microorganisms passing through.

1 ml of nebulised *E. coli* K12 was passed through the device with the lamp switched off. The rate of air flow was 40 liters per minute. This was repeated with the lamp switched on. Bacterial stock and collected samples were diluted and plated out on agar plates (L-Agar, no antibiotics). L-Agar can be prepared using 10 g Tryptone, 5 g yeast extract, 5 g NaCl, 15 g bacto-agar, made up to 1 liter with distilled water; autoclaved at 15 psi for 30 minutes at 121° C. to melt and sterilize; and agar plates can be poured at 20 ml of agar per plate, for example in a Petri dish. The plates were incubated at 37° C. overnight and colonies counted.

The bacterial counts were: Bacteria applied: $8.25 \times 10^9$
Bacteria collected without UV applied: $1.37 \times 10^7$
Bacteria collected with UV applied: $9.1 \times 10^5$ This is equivalent to approximately 93% sterilisation by the UV, or 99.99% sterilisation overall.

A repeat experiment gave approximately 98.8% sterilisation by the UV. Hence, even with this 'rough and ready' version of the device, the target sterilisation of approximately 95% was achieved. Less than 0.2% of the starting bacteria passed through the device alive in the absence of applied UV suggesting a poor delivery of inactivated microorganism with applied UV although some of this loss could be due to the action of the nebuliser (see below).

Example 3

This example illustrates the advantages of reducing obstruction and allowing streamlined flow.

A device was constructed comprising a 5 cm diameter quartz tube with UV lamps mounted on the outside of the tube to simulate the UV irradiation due to closer lamps within the tube. The ends of the tube were sealed with bungs through which connections were made to inlet and output connecting tubes.

When tested with Coomassie blue dye, little or no aerosol was deposited on the walls of the sterilising chamber (i.e. quartz tube), although there was evidence of some deposition on the end bungs.

As some loss of the live bacteria may be expected by the process of nebulisation, nebulised sample was passed directly through 1000 ml PBS to collect and analyse loss. Bacteria were also passed through the device with the lamps off (i.e. absence of applied UV) and collected in PBS. Finally, bacteria were passed through the device with the lamps on (i.e. applied UV).

In each case 2 ml of *E. coli* bacteria were nebulised with an Aeroneb Lab nebuliser manufactured by Aerogen, and collected in 1000 ml PBS. These samples were diluted and plated out on agar plates (2 plates per dilution, L-Agar, no antibiotics) and incubated overnight at 37° C. Colonies were counted and colonies per ml calculated. The results are shown in Table 3 (below)

TABLE 3

Sterilization of *E. coli* following exposure to UV irradiation and/or nebulisation.

| Nebulised | UV irradiated | cfu per ml | % original sample | % nebulised sample | % sterilisation by UV |
|---|---|---|---|---|---|
| No | No | $4.3 \times 10^5$ | 100 | — | — |
| Yes | No | $1.76 \times 10^5$ | 41 | — | — |
| Yes | No | $6.7 \times 10^4$ | 15.6 | 38 | — |
| Yes | Yes | $3.25 \times 10^3$ | 0.8 | 1.8* | 95 |

*= 98% sterilisation overall
cfu—colony forming units

Owing to the large size of the device, a longer tube was required to link the tube to the nebuliser and collection/testing equipment in a sterile cabinet. This probably significantly contributed to the loss of 60% of the nebulised sample through the device with the lamps off. Nevertheless, 95% sterilization of the nebulised sample by the UV lamps (98% sterilisation overall) confirms the effectiveness of the device and achieves accepted standards. Passing of 38% of the nebulised sample through the device with the lamps off (i.e. absence of applied UV) represents significant delivery of inactivated material when the lamps are on.

Example 4

This example illustrates a practical portable version of the device.

A device according to FIG. 4. was constructed. The main chamber was constructed from an aluminum tube (5 cm diameter) which was internally polished to provide an effective reflector. Airflow is less obstructed compared to Example 2 by having the lamp connectors at the ends of the chamber, and having the air inlet and outlet offset from these ends. Since the tube lacks corners or obstruction to the air flow from the lamp holders, it is expected to be more effective at allowing the passage of inactivated microorganisms. Initial testing suggests that this lets microorganisms through.

The invention claimed is:

1. A protective device for protection against infection from airborne microorganisms comprising a disinfection chamber in fluid communication with a face mask wherein the chamber is arranged to disinfect or sterilize fluid in the chamber by exposure to a UV source prior to discharge of the fluid from the chamber, wherein the UV source is selected from one of a fluorescent lamp or a light emitting diode, said UV source emitting UV radiation in the range of from 240 nm to 300 nm and an intensity of 75 W/m² to 350 W/m², and wherein the dose of UV radiation delivered to the fluid by said UV source is in the range of 5-200 J/m².

2. The protective device according to claim 1, wherein the chamber is arranged to disinfect or sterilize fluid in the chamber prior to discharge of the fluid from the chamber to the mask.

3. The protective device according to claim 1, wherein the fluid comprises a defective-interfering (DI) virus.

4. The protective device according to claim 1, wherein the device is adapted for carrying by the user.

5. The protective device according to claim 1, wherein the chamber is arranged to disinfect or sterilize fluid in the chamber prior to discharge of the fluid from the chamber to the external environment.

6. The protective device according to claim 1, configured to provide a substantially constant disinfection or sterilization level.

7. The protective device according to claim 6, wherein
the substantially constant disinfection or sterilization level
is achieved by providing at least one of variable levels of shading to the UV source and variable levels of UV intensity, and
an increase in air-flow into the chamber is associated with at least one of a decrease in the level of shading of the UV source and an increase in the intensity of the UV source.

8. The device of claim 1, wherein the dose of UV radiation is in the range of 30-90 $J/m^2$.

9. The device according to claim 1, wherein the fluid discharged from the chamber comprises inactive microorganisms comprising antigen.

10. The device according to claim 9, wherein the antigen is capable of conferring immune protection on a recipient of the fluid.

* * * * *